United States Patent [19]

Branca et al.

[11] 4,377,522
[45] Mar. 22, 1983

[54] BENZODIAZEPINE DERIVATIVES

[75] Inventors: Quirico Branca, Basel; Albert E. Fischli; André Szente, both of Riehen, all of Switzerland

[73] Assignee: Hoffmann-La Roche Inc., Nutley, N.J.

[21] Appl. No.: 280,644

[22] Filed: Jul. 6, 1981

[30] Foreign Application Priority Data

Jul. 31, 1980 [CH] Switzerland ............... 5842/80

[51] Int. Cl.³ ............................................. C07D 243/24
[52] U.S. Cl. ........................ 260/239.3 D; 424/248.54; 424/250; 424/274; 424/273 R; 424/244; 564/50; 260/239 B; 544/393; 544/166; 548/308; 548/559
[58] Field of Search ........................... 260/239.3 D

[56] References Cited

U.S. PATENT DOCUMENTS 3,429,874  2/1969  Topliss ............... 260/239.3 D
4,251,443  2/1981  Fischli et al. ......... 260/239.3 D Primary Examiner—Robert T. Bond
Attorney, Agent, or Firm—Jon S. Saxe; Bernard S. Leon; Frank P. Hoffman

[57] ABSTRACT

There are presented novel benzodiazepine derivatives of the formula

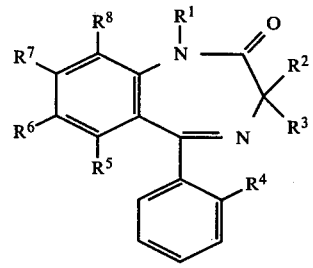

wherein $R^1$ is lower alkyl, lower hydroxyalkyl or lower dialkylaminoalkyl, $R^2$ and $R^3$ each are lower alkyl, $R^4$ is halogen, $R^5$, $R^7$ and $R^8$ each are hydrogen or halogen and $R^6$ is nitro, amino, lower alkylamino, lower dialkylamino or a group of the formula $H_2N-C(CH_3)_2-CO-NH-$, $R^9R^{10}N-CO-NH-$ or

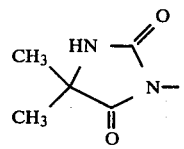

and either $R^9$ is hydrogen or lower alkyl and $R^{10}$ is lower alkyl or lower hydroxyalkyl or $R^9$ and $R^{10}$ together with the nitrogen atom are a 3- to 7-membered heterocycle which, provided it is at least 5-membered, can contain as a ring member an oxygen or sulfur atom or a group of the formula $>N-R$ in which R is hydrogen or lower alkyl, and their pharmaceutically acceptable acid addition salts.

The compounds possess aldosterone-antagonistic properties and are accordingly suitable for the control or prevention of heart failure, hepatic ascites, primary aldosteronism and idiopathic hypertension.

13 Claims, No Drawings

BENZODIAZEPINE DERIVATIVES

DESCRIPTION OF THE INVENTION

The present invention is concerned with benzodiazepine derivatives. More particularly, the invention is concerned with 3,3-dialkylbenzodiazepine derivatives of the formula

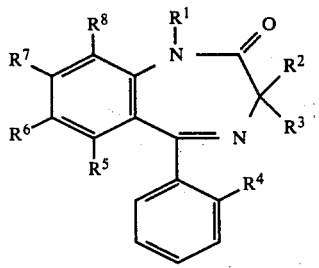

I wherein $R^1$ is lower alkyl, lower hydroxyalkyl or lower dialkylaminoalkyl, $R^2$ and $R^3$ each are lower alkyl, $R^4$ is halogen, $R^5$, $R^7$ and $R^8$ each are hydrogen or halogen and $R^6$ is nitro, amino, lower alkylamino, lower dialkylamino or a group of the formula $H_2N-C(CH_3)_2-CO-NH-$, $R^9R^{10}N-CO-NH-$ or

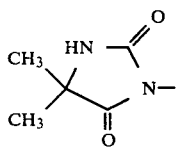

and either $R^9$ is hydrogen or lower alkyl and $R^{10}$ is lower alkyl or lower hydroxyalkyl or $R^9$ and $R^{10}$ together with the nitrogen atom are a 3- to 7-membered heterocycle which, provided it is at least 5-membered, can contain as a ring member an oxygen or sulfur atom or a group of the formula $>N-R$ in which R is hydrogen or lower alkyl,
and their pharmaceutically acceptable acid addition salts.

These compounds exhibit aldosterone-antagonistic properties and are suitable for the control or prevention of heart failure, hepatic ascites, primary aldosteronism and idiopathic hypertension.

The term "lower alkyl", taken alone or in combinations such as in "lower hydroxyalkyl", "lower dialkylaminoalkyl", "lower alkylamino", "lower dialkylamino" and the like denotes straight-chain or branched-chain saturated hydrocarbon groups containing at most 7, preferably at most 4, carbon atoms such as methyl, ethyl, n-propyl, isopropyl, n-butyl, t-butyl etc. The term "lower alkylene" as used in the present description denotes divalent saturated hydrocarbon groups containing at most 7, preferably at most 4, carbon atoms, which groups can be straight-chain or branched such as methylene, ethylene, 1,2-propylene, ethylidene and the like. The term "lower hydroxyalkyl" includes groups such as 2-hydroxyethyl, 3-hydroxy-2-propyl and the like. The term "lower dialkylaminoalkyl" includes groups such as 2-diethylaminoethyl, 2-dimethylaminoethyl, 3-(methyl-ethylamino)-butyl and the like. The term "lower alkylamino" signifies, for example, methylamino, ethylamino, isopropylamino, n-butylamino and the like. The term "lower dialkylamino" denotes groups such as dimethylamino, diethylamino, diisopropylamino and the like. The term "halogen" signifies fluorine, chlorine, bromine or iodine.

The term "heterocycle" as defined more precisely above signifies hetereocyclic groups such as aziridin-1-yl, pyrrolidin-1-yl, 4-methyl-piperazin-1-yl, morpholin-4-yl and the like.

Preferred among the compounds which are embraced by formula I are those wherein $R^1$ is methyl. $R^2$ and $R^3$ both preferably are methyl. $R^4$ preferably is fluorine or chlorine. The preferred meaning of $R^5$ is hydrogen, chlorine or bromine. $R^7$ preferably is hydrogen, chlorine or bromine. The meanings hydrogen and chlorine are preferred for $R^8$.

Especially preferred compounds embraced by formula I are those wherein $R^1$, $R^2$ and $R^3$ all are methyl.

Quite especially preferred compounds of formula I are:
7-Amino-9-chloro-5-(o-fluorophenyl)-1,3-dihydro-1,3,3-trimethyl-2H-1,4-benzodiazepin-2-one;
7-amino-6,8-dibromo-5-(o-chlorophenyl)-1,3-dihydro-1,3,3-trimethyl-2H-1,4-benzodiazepin-2-one;
7-amino-6,8-dibromo-5-(o-fluorophenyl)-1,3-dihydro-1,3,3-trimethyl-2H-1,4-benzodiazepin-2-one and
7-amino-6,8-dichloro-5-(o-chlorophenyl)-1,3-dihydro-1,3,3-trimethyl-2H-1,4-benzodiazepin-2-one.

Other preferred compounds of formula I are: 1-[6-Bromo-5-(o-chlorophenyl)-2,3-dihydro-1,3,3-trimethyl-2-oxo-1H-1,4-benzodiazepin-7-yl]-3-(2-hydroxyethyl)urea;
7-amino-9-chloro-5-(o-chlorophenyl)-1,3-dihydro-1,3,3-trimethyl-2H-1,4-benzodiazepin-2-one;
1-[5-(o-chlorophenyl)-2,3-dihydro-1,3,3-trimethyl-2-oxo-1H-1,4-benzodiazepin-7-yl]-3-(2-hydroxyethyl)urea;
7-amino-6,8,9-trichloro-1,3-dihydro-5-(o-fluorophenyl)-1,3,3-trimethyl-2H-1,4-benzodiazepin-2-one;
7-amino-8,9-dichloro-5-(o-fluorophenyl)-1,3-dihydro-1,3,3-trimethyl-2H-1,4-benzodiazepin-2-one;
7-amino-6-chloro-5-(o-fluorophenyl)-1,3-dihydro-1,3,3-trimethyl-2H-1,4-benzodiazepin-2-one and
2-amino-N-[5-(o-fluorophenyl)-2,3-dihydro-1,3,3-trimethyl-2-oxo-1H-1,4-benzodiazepin-7-yl]-2-methylpropionamide.

The novel 3,3-dialkylbenzodiazepin derivatives of formula I and their pharmaceutically acceptable acid addition salts can be manufactured in accordance with the invention by (a) cyclising a compound of the formula

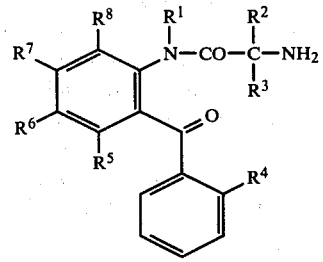

II wherein $R^1$, $R^2$, $R^3$, $R^4$, $R^5$, $R^6$, $R^7$ and $R^8$ are as above, or (b) cleaving off the protecting group(s) from a compound of the formula

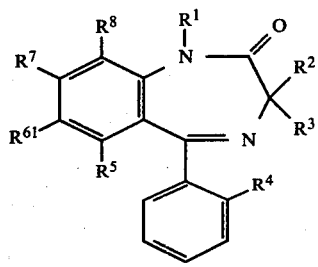

wherein $R^1$, $R^2$, $R^3$, $R^4$, $R^5$, $R^7$ and $R^8$ are as above and $R^{61}$ is protected lower alkylamino or a group of the formula $ZZ'N—$, $Z—NH—C(CH_3)_2—CO—NH—$ or $R^{91}R^{101}N—CO—NH—$ and either $R^{91}$ is hydrogen or lower alkyl and $R^{101}$ is a group of the formula $—A—O—Z$ or $R^{91}$ is a protecting group and $R^{101}$ is lower alkyl or a group of the formula $—A—O—Z$, or $R^{91}$ and $R^{101}$ together with the nitrogen atom are a 5- to 7-membered heterocycle which contains as a ring member a group of the formula $>N—R^{01}$, in which $R^{01}$ is a protecting group, and A is lower alkylene and Z and Z' each are a protecting group, whereby Z and Z' together can be a single protecting group, or (c) reacting a 3,3-dialkylbenzodiazepine derivative of the formula

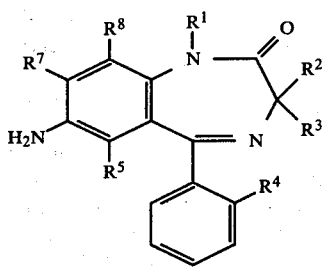

wherein $R^1$, $R^2$, $R^3$, $R^4$, $R^5$, $R^7$ and $R^8$ are as above with a halide of the formula $$R^{92}R^{102}N—CO—X \qquad IV$$

wherein X is halogen and either $R^{92}$ and $R^{102}$ each are lower alkyl or $R^{92}$ and $R^{102}$ together with the nitrogen atom are a 3- to 7-membered heterocycle which, provided it is at least 5-membered, can contain as a ring member an oxygen or sulphur atom or a group of the formula $>N—R^{02}$ in which $R^{02}$ is lower alkyl, or (d) reacting a 3,3-dialkylbenzodiazepine derivative of the above formula Ia with an isocyanate of the formula $$R^{93}—NCO \qquad V$$

wherein $R^{93}$ is lower alkyl, or (e) reacting a compound of the formula

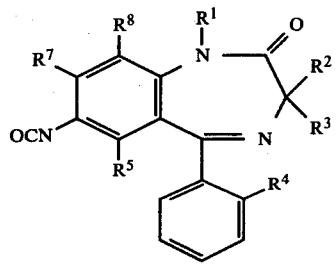

wherein $R^1$, $R^2$, $R^3$, $R^4$, $R^5$, $R^7$ and $R^8$ are as above, with an amino compound of the formula $$R^9R^{10}NH \qquad VII$$

wherein $R^9$ and $R^{10}$ are as above, or (f) treating a compound of the formula

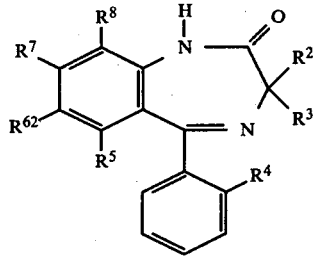

wherein $R^2$, $R^3$, $R^4$, $R^5$, $R^7$ and $R^8$ are as above and $R^{62}$ is nitro or lower dialkylamino, with an alkylating agent yielding the group $R^1$, or (g) halogenating a 3,3-dialkylbenzodiazepine derivative of the formula

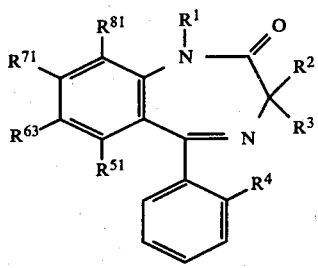

wherein $R^1$, $R^2$, $R^3$ and $R^4$ are as above and either $R^{63}$ is nitro and $R^{51}$, $R^{71}$ and $R^{81}$ all are hydrogen or $R^{63}$ is amino or lower alkylamino and $R^{81}$ is hydrogen or halogen, and one of $R^{51}$ and $R^{71}$ is hydrogen and the other is hydrogen or halogen, or (h) converting the primary amino group in a 3,3-dialkylbenzodiazepine derivative of the above formula Ia into the nitro group, or (i) reducing the nitro group in a 3,3-dialkylbenzodiazepine derivative of the formula

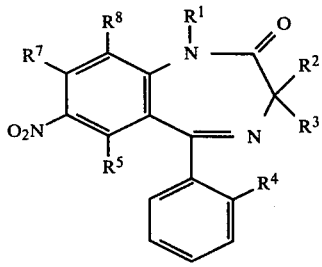

Ic wherein $R^1$, $R^2$, $R^3$, $R^4$, $R^5$, $R^7$ and $R^8$ are as above, to the amino group, or (j) monoalkylating or dialkylating the primary amino group in a 3,3-dialkylbenzodiazepine derivative of the above formula Ia, or (k) alkylating the secondary amino group in a 3,3-dialkylbenzodiazepine derivative of the formula

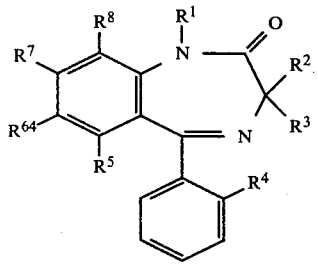

Id wherein $R^1$, $R^2$, $R^3$, $R^4$, $R^5$, $R^7$ and $R^8$ are as above and $R^{64}$ is lower alkylamino,
or (l) reacting a 3,3-dialkylbenzodiazepine derivative of the above formula Ia with a dihalide of the formula

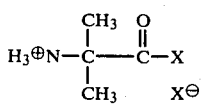

wherein X is as above
or (m) treating a 3,3-dialkylbenzodiazepine derivative of the formula

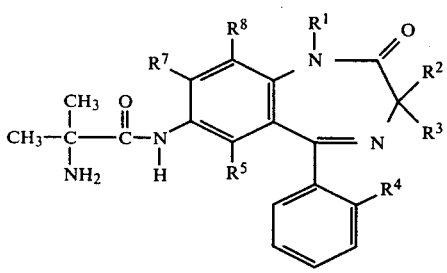

Ie wherein $R^1$, $R^2$, $R^3$, $R^4$, $R^5$, $R^7$ and $R^8$ are as above, with phosgene, or (n) hydrolytically opening the aziridine ring in a 3,3-dialkylbenzodiazepine derivative of the formula

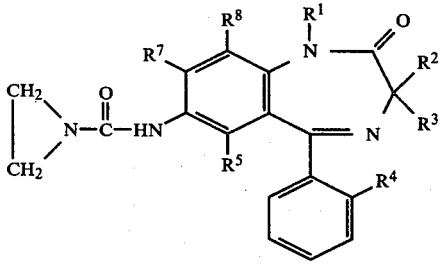

If wherein $R^1$, $R^2$, $R^3$, $R^4$, $R^5$, $R^7$ and $R^8$ are as above, or (o) converting a 3,3-dialkylbenzodiazepine derivative of the formula I into a pharmaceutically acceptable acid addition salt.

In accordance with embodiment (a) of the process, a 3,3-dialkylbenzodiazepine derivative of formula I can be manufactured by cyclising a compound of formula II. This cyclisation is carried out very readily and can be expedited, if necessary, by standing for a long time and/or by applying of heat. The cyclisation can be carried out in neutral, alkaline or acidic medium. The cyclisation is conveniently carried out in an inert organic solvent; for example, in hydrocarbons such as benzene, toluene etc, in chlorinated hydrocarbons such as chloroform, methylene chloride etc, in ethers such as dioxan, etc. Suitable temperatures for the cyclisation of compounds of formula II are temperatures in the range between room temperature and about 150° C. depending, of course, on the solvent which is used. In a preferred embodiment there are used conditions which enable the water which is formed in the cyclisation to be azeotropically removed.

The compounds of formula II need not necessarily be used in isolated form and in many cases this is even not possible. Generally, it has been found to be convenient to cyclise the compounds of formula II directly or to leave them to cyclise without isolation from the reaction mixture in which they have been prepared.

In accordance with embodiment (b) of the process, a 3,3-dialkylbenzodiazepine derivative of formula I can be manufactured by removing the protecting group or the protecting groups from a benzodiazepine derivative of formula III. Suitable nitrogen-protecting groups for the purpose of the present invention are primarily acyl groups, preferably readily cleavable alkoxycarbonyl or aralkoxycarbonyl groups, especially the t-butoxycarbonyl group, the benzyloxycarbonyl group etc, as well as readily cleavable aralkyl groups such as the benzyl group. Suitable oxygen-protecting groups are on the one hand acyl groups or aralkyl groups such as those mentioned above as nitrogen-protecting groups and on the other hand acetal and ketal protecting groups such as tetrahydro-2-pyranyl, 2-methoxy-2-propyl, methoxymethyl, β-methoxyethoxy-methyl etc, readily cleavable alkyl groups such as t-butyl etc or alkanoyl groups such as acetyl and the like.

The removal of the protecting group or of the protecting groups from the benzodiazepine derivatives of formula III is carried out according to methods known per se, whereby, of course, the nature of the protecting group or protecting groups to be removed must be taken into consideration when choosing the method or methods used for the removal. In addition, it will, of course, be appreciated that only those methods can be used which selectively remove the protecting group or protecting groups without affecting other structural elements present in the molecule.

The groups mentioned above as examples of protecting groups can be cleaved off, depending on their nature, hydrogenolytically and/or hydrolytically. Thus, for example, the benzyloxycarbonyl group and the t-butoxycarbonyl group can be cleaved off under selective acidic conditions; for example, by treatment with a mixture of hydrogen bromide and glacial acetic acid or by treatment with boron trifluoride or boron tribromide in an inert organic solvent such as dichloromethane. The t-butoxycarbonyl group can also be cleaved off by treatment with hydrogen chloride in an inert organic solvent such as dioxan, tetrahydrofuran or the like or by treatment with trifluoroacetic acid. The tetrahydropyranyl group can be cleaved off under mild acidic conditions; for example, by treatment with dilute aqueous mineral acid or by transacetalisation with a lower alcohol such as, for example, methanol or ethanol in the presence of an acidic catalyst such as, for example, hydrochloric acid, p-toluenesulphonic acid, pyridinium p-toluenesulphonate or the like. The t-butyl group can be cleaved off, for example, using trifluoroacetic acid. The benzyl group can be cleaved off by catalytic hydrogenation (e.g. over palladium/carbon). The acetyl group can be cleaved off under mild alkaline conditions; for example, with a solution of a sodium alcoholate in the corresponding alcohol (e.g. methanolic sodium methylate).

If Z and Z' in compounds of formula III, wherein $R^{61}$ signifies a group of the formula ZZ'N—, signify a single protecting group, then there primarily come into consideration cyclic imides (e.g. phthalimides). Such a protecting group can be readily cleaved off (e.g. with hydrazine).

In accordance with embodiment (c) of the process, a 3,3-dialkylbenzodiazepine derivative of formula I can be manufactured by reacting a benzodiazepine derivative of formula Ia with a halide of formula IV. This reaction is carried out in the presence of an acid-binding agent; for example, an inorganic base such as potassium carbonate, sodium carbonate etc or an organic base such as a tertiary amino compound (e.g. triethylamine, N-ethyl-diisopropylamine, quinuclidine and the like).

The reaction of the compounds of formulae Ia and IV is conveniently carried out at room temperature or at a temperature below room temperature; it proceeds relatively slowly and generally takes several days.

In accordance with embodiment (d) of the process, a 3,3-dialkylbenzodiazepine derivative of formula I can be manufactured by reacting a benzodiazepine derivative of formula Ia with an isocyanate of formula V. This reaction is conveniently carried out in an organic solvent which is inert under the reaction conditions; for example, in a halogenated hydrocarbon such as, for example, methylene chloride, dichloroethane, chloroform or o-dichlorobenzene, in an ether such as, for example, tetrahydrofuran, dioxan, dimethoxyethane or diethyleneglycol dimethyl ether, or the like. In many cases it has been found to be favourable to carry out the reaction in the presence of a catalytically-acting small amount of a base; for example, in the presence of a tertiary amino compound such as triethylamine, N-ethyl-diisopropylamine, quinuclidine etc. The temperature at which the reaction is carried out is not critical and the reaction can therefore be carried out at room temperature or at a temperature below room temperature or above room temperature (e.g. at the reflux temperature).

In accordance with embodiment (e) of the process, a 3,3-dialkylbenzodiazepine derivative of formula I can be manufactured by reacting a benzodiazepine derivative of formula VI with an amino compound of formula VII. In this case, the benzodiazepine derivative of formula VI is conveniently prepared in the manner described below from the corresponding benzodiazepine derivative of formula Ia shortly or immediately before the reaction with the amino compound of formula VII and is introduced into the reaction not in isolated form but in the solution in which it has previously been prepared from the corresponding benzodiazepine derivative of formula Ia.

An amino compound of formula VII can then be added to the aforementioned solution containing the benzodiazepine derivative of formula VI. In so doing, the amino compound can be used in the form of a solution or also in the absence of a solvent. Where an amino compound which is gaseous at room temperature is used (e.g. in the case of methylamine), it can be introduced as the gas into the aforementioned solution containing the isocyanate of formula VI.

On the other hand, it is also possible to add the aforementioned solution of the isocyanate of formula VI to the amino compound, conveniently in the form of a solution.

In many cases it is convenient to use an excess of the amino compound of formula VII and this is indeed necessary when it contains more than one nitrogen atom which is capable of reacting with an isocyanate group (e.g. in the case of piperazine).

Various organic solvents which are inert under the reaction conditions (e.g. halogenated hydrocarbons such as, for example, dichloroethane, methylene chloride, chloroform and o-dichlorobenzene and ethers such as, for example, tetrahydrofuran, dioxan, dimethoxyethane and diethyleneglycol dimethyl ether or the like) are suitable as the solvent for embodiment (e) of the process.

The reaction of a benzodiazepine derivative of formula VI with an amino compound of formula VII is conveniently carried out at room temperature or at a temperature below room temperature. When the amino compound of formula VII is added to a solution of the isocyanate of formula VI, the addition should be performed within a short time, whereas in the opposite case (i.e. when the solution of the isocyanate of formula II is added to the amino compound of formula VII then the promptness with which the addition is carried out plays no essential role.

In accordance with embodiment (f) of the process, a 3,3-dialkylbenzodiazepine derivative of formula I can be manufactured by treating a compound of formula VIII with an alkylating agent which yields the group $R^1$. Any suitable alkylating agent can be used for the present process embodiment. In this case, there are conveniently used halides such as, for example, methyl iodide, ethyl iodide, isopropyl bromide, n-propyl bromide, n-butyl bromide, 2-bromoethanol, N,N-diethylamino-ethyl chloride and the like, dialkyl sulphates such as, for example, dimethyl sulphate and diethyl sulphate, or the like, and the reaction is carried out in an inert organic solvent; for example, in an ether such as, for example, tetrahydrofuran, dioxan and diethyl ether or in acetone, N,N-dimethylformamide or the like in the presence of an acid-binding agent such as, for example, potassium and sodium carbonate, conveniently at room temperature.

In accordance with embodiment (g) of the process, a 3,3-dialkylbenzodiazepine derivative of formula I can be manufactured by halogenating a compound of formula Ib. Convenient halogenating agents, which can be used are compounds such as N-chloro-succinimide, N-bromo-succinimide, N-chloro-acetamide and the like. Suitable solvents for the present process aspect are primarily halogenated hydrocarbons such as, for example, methylene chloride, 1,2-dichloroethane, chloroform and the like or other inert organic solvents such as, for example, acetonitrile, ether etc. However, aqueous systems such as, for example, mixtures of concentrated hydrochloric acid and formic acid and the like can also be used. The halogenation is preferably carried out at a temperature of about 0° C. to room temperature, conveniently at room temperature.

Other suitable halogenating agents are elemental halogens such as chlorine gas and bromine. In this case, the halogenation is preferably carried out in acidic aqueous solution, whereby in many cases the corresponding hydrogen halide is conveniently used as the acid, at temperatures of about −10° to +10° C., preferably at 0° C., or in an acidic organic solvent such as, for example, formic acid, acetic acid and the like, conveniently at room temperature, or at a temperature below room temperature or above room temperature.

In accordance with embodiment (h) of the process, a 3,3-dialkylbenzodiazepine derivative of formula I can be manufactured by converting the primary amino group in a compound of formula Ia into the nitro group. For example, a diazonium salt such as the corresponding diazonium tetrafluoroborate, which is readily accessible from the amine of formula Ia and need not be isolated, can be reacted with a nitrite such as sodium nitrite, and a copper (I) salt. This reaction is conveniently carried out in water at a temperature of about −10° C. to room temperature.

An amino compound of formula Ia can, however, also be converted into the corresponding nitro compound by oxidation. Hydrogen peroxide in acetic acid and a catalytic amount of a mineral acid such as sulphuric acid is conveniently used as the oxidising agent. Other suitable oxidising agents are, for example, peracetic acid, perbenzoic acid, trifluoroperacetic acid and the like. The reaction conditions which are necessary can be readily ascertained by any person skilled in the art.

In accordance with embodiment (i) of the process, a 3,3-dialkylbenzodiazepine derivative of formula I can be manufactured by reducing the nitro group in a compound of formula Ia to the amino group. The reduction is conveniently carried out using a reducing agent such as tin (II) chloride, tin, zinc and the like in acidic aqueous medium (e.g. in aqueous hydrochloric acid, concentrated hydrochloric acid or the like) at a temperature in the range of about 0° C. to room temperature.

In accordance with embodiment (j) of the process, a 3,3-dialkylbenzodiazepine derivative of formula I can be manufactured by monoalkylating or dialkylating the primary amino group in a compound of formula Ia. The alkylating agent can be a halide such as methyl iodide, isopropyl bromide or n-butyl bromide or a dialkyl sulphate such as dimethyl sulphate or diethyl sulphate in combination with an acid-binding agent such as potassium carbonate, sodium carbonate, triethylamine, quinuclidine and the like or an aldehyde or ketone such as formaldehyde, acetaldehyde or acetone in combination with a reducing agent such as formic acid.

The alkylation is conveniently carried out in an organic solvent which is inert under the reaction conditions such as acetonitrile, diethyl ether, tetrahydrofuran, dimethoxyethane and the like. If the reaction is carried out using an aldehyde or ketone in the presence of a reducing agent, then formic acid is conveniently used as the solvent and reducing agent. The temperature at which the present process aspect is carried out is not critical. Therefore, this alkylation can be carried out at room temperature or at a temperature below room temperature or above room temperature (e.g. at the boiling point of the reaction mixture).

In accordance with embodiment (k) of the process, a 3,3-dialkylbenzodiazepine derivative of general formula I can be manufactured by alkylating the secondary amino group in a compound of formula Id. This reaction can be carried out in analogy to the monoalkylation or dialkylation of compounds of formula Ia in accordance with embodiment (j) of the process.

In accordance with embodiment (1) of the process, a 3,3-dialkylbenzodiazepine derivative of formula I can be manufactured by reacting a compound of formula Ia with a dihalide of formula IX. This reaction is conveniently carried out in an inert organic solvent such as tetrahydrofuran, dioxan, acetonitrile, dimethylformamide and the like in the presence of an acid-binding agent such as potassium carbonate, sodium carbonate, triethylamine, pyridine, quinuclidine and the like. Preferably, the reaction is carried out at room temperature, although it can, however, also be carried out at a temperature below room temperature (e.g. at 0°C.) or above room temperature.

In accordance with embodiment (m) of the process, a 3,3-dialkylbenzodiazepine derivative of formula I can be manufactured by treating a compound of formula Ie with phosgene. Especially suitable solvents for the present process embodiment are halogenated hydrocarbons such as methylene chloride, chloroform, 1,2-dichloroethane and the like. Other suitable solvents are ethers such as t-butyl methyl ether, tetrahydrofuran and the like, acetonitrile, benzene, dimethylformamide etc. The reaction is preferably carried out at a temperature in the range of about 0° C. to room temperature.

In accordance with embodiment (n) of the process, a 3,3-dialkylbenzodiazepine derivative of formula I can be manufactured by hydrolytically opening the aziridine ring in a compound of formula If.

This hydrolytic ring-opening is carried out under acidic conditions, where coming into consideration only those acids whose anion does not react with the aziridine ring. The hydrolytic ring-opening is conveniently carried out in the presence of a suitable organic solvent which is inert under the reaction conditions and at room temperature. For example, the reaction can be carried out by dissolving the compound of formula If in dioxan or the like, adding to the solution a small amount of a mineral acid (e.g. a few drops of 25% sulphuric acid) and leaving the mixture to stand for a further short time (e.g. 15 to 30 minutes).

In accordance with embodiment (o) of the process, the 3,3-dialkylbenzodiazepine derivatives of formula I can be converted into pharmaceutically acceptable acid addition salts. The manufacture of such pharmaceutically acceptable acid addition salts is carried out according to generally customary methods. There come into consideration not only salts with inorganic acids but also salts with organic acids; for example, hydrochlorides, hydrobromides, sulphates, citrates, acetates, succinates, methanesulphonates, p-toluenesulphonates and the like.

The compounds of formula II used as starting materials can be prepared according to methods known per se. Conveniently, compounds of formula II are prepared from compounds of the formula

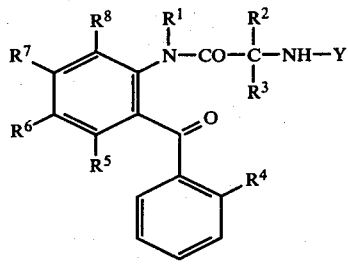

X wherein $R^1, R^2, R^3, R^4, R^5, R^6, R^7$ and $R^8$ are as above and Y is a protecting group, there coming into consideration as protecting groups primarily acyl groups, preferably readily cleavable alkoxycarbonyl or aralkoxycarbonyl groups, especially the benzyloxycarbonyl group, which can be cleaved off under mild acidic conditions, for example with hydrogen bromide in glacial acetic acid or with boron trifluoride or boron tribromide in an inert organic solvent such as methylene chloride or the like. By removing the protecting group denoted by Y from compounds of formula X there are obtained compounds of formula II.

Compounds of formula X can also be prepared according to methods known per se. For example, a compound of the formula

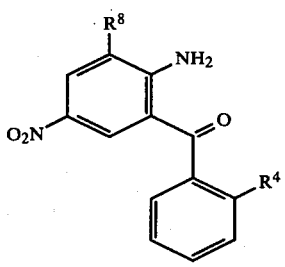

XI wherein $R^4$ and $R^8$ are as above,
can be reacted, in analogy to embodiment (1) of the process, with a dihalide of the formula

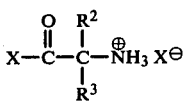

XII wherein $R^2, R^3$ and X are as above,
to give a compound of the formula

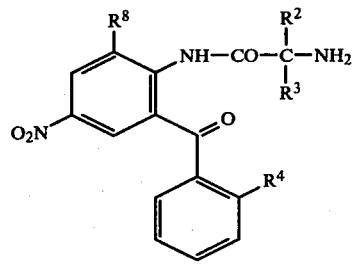

XIII wherein $R^2, R^3, R^4$ and $R^8$ are as above.

After protecting the primary amino group present in a compound of formula XIII with a suitable reagent which yields the group Y such as chloroformic acid benzyl ester or the like and alkylating the resulting compound with an alkylating agent which yields the group $R^1$ in analogy to embodiment (f) of the process, there is obtained a compound of the formula

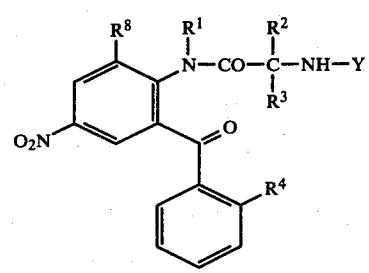

Xa wherein $R^1, R^2, R^3, R^4, R^8$ and Y are as above.

By reducing a compound of formula Xa in analogy to embodiment (i) of the process and, if desired, halogenating the resulting amino compound in analogy to embodiment (g) of the process there is obtained a compound of the formula

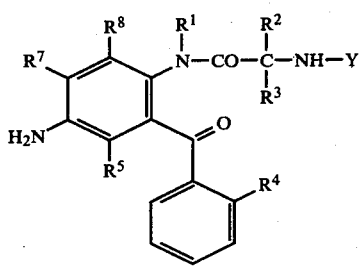

Xb wherein $R^1, R^2, R^3, R^4, R^5, R^7, R^8$ and Y are as above.

In analogy to embodiments (c), (d), (e), (h), (i), (k), (l), (m) and (n) of the process described above and to the preparation of the starting materials required for these described below, compounds of formula Xb can be converted into compounds of formula X wherein $R^6$ is nitro, lower alkylamino, lower dialkylamino, or a group of the formula $R^9R^{10}N-CO-NH-$, $H_2N-C(CH_3)_2-CO-NH-$ or

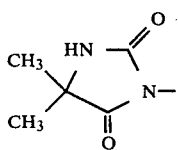

and $R^9$ and $R^{10}$ are as above.

Compounds of formula II can, however, also be prepared by cleaving off the protecting group denoted by Y from a compound of the formula

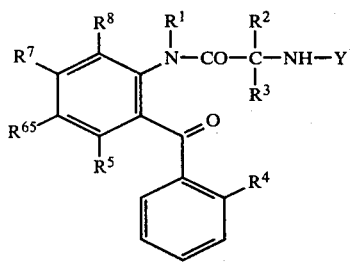

XIV wherein $R^{65}$ is protected lower alkylamino or a group of the formula $Z-NH-C(CH_3)_2-CO-NH-$ or $R^{91}R^{101}N-CO-NH-$, and $R^1$, $R^2$, $R^3$, $R^4$, $R^5$, $R^7$, $R^8$, $R^{91}$, $R^{101}$, Y and Z are as above, and, previously or in the same operation, cleaving off the protecting groups present in the group $R^{65}$ in analogy to embodiment (b) of the process.

Compounds of formula XIV can be obtained in a manner known per se from compounds of formula Xb. For example, a compound of formula Xb can be reacted with a carbamoyl halide of the formula

 XV wherein either $R^{93}$ is a protecting group and $R^{103}$ is lower alkyl or a group of the formula $-A-O-Z$ or $R^{93}$ and $R^{103}$ together with the nitrogen atom are a 5- to 7-membered heterocycle which contains as a ring member a group of the formula $>N-R^{01}$ and A,X,Z and $R^{01}$ are as above, in analogy to embodiment (c) of the process or with an isocyanate of the formula

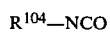 XVI wherein $R^{104}$ is a group of the formula $-A-O-Z$ and A and Z are as above, in analogy to embodiment (d) of the process or with a carboxylic acid halide of the formula

 XVII wherein X and Z are as above, in analogy to embodiment (1) of the process or an isocyanate of the formula

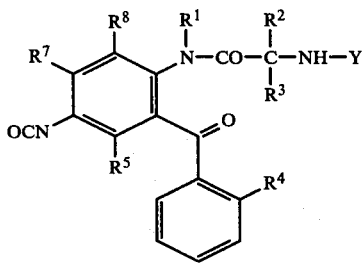

XVIII wherein $R^1$, $R^2$, $R^3$, $R^4$, $R^5$, $R^7$, $R^8$ and Y are as above, which can be prepared from an amine of formula Xb in analogy to the preparation of compounds of formula VI from compounds of formula Ia described below, can be reacted with an amine of the formula

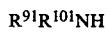 XIX wherein $R^{91}$ and $R^{101}$ are as above, in analogy to embodiment (e) of the process or the amino group in a compound of formula Xb can be protected with an agent which yields the group Z and the resulting compound can be alkylated in analogy to embodiment (f) or (j) of the process depending on the nature of the protecting group.

A further possibility for the preparation of compounds of formula II comprises converting a nitrobenzophenone derivative of formula XI into a compound of the formula

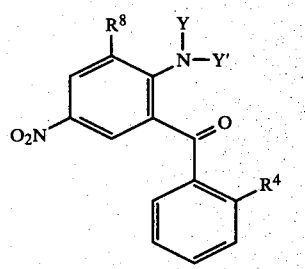

XX wherein $R^4$, $R^8$ and Y are as above and Y' is hydrogen or a protecting group, whereby Y and Y' together can be a single protecting group, thereupon reducing the nitro group in analogy to embodiment (i) of the process and, if desired, halogenating a thus-obtained compound in analogy to embodiment (g) of the process. The compounds obtained in the manner just described correspond to the formula

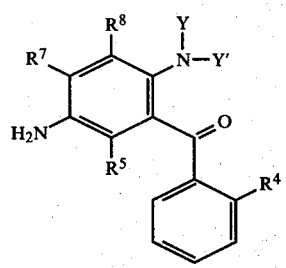

XXI wherein $R^4$, $R^5$, $R^7$, $R^8$, Y and Y' are as above.

A compound of the above formula XXI can then be converted according to methods which are known per se and which are to some extent described above into a compound of the formula

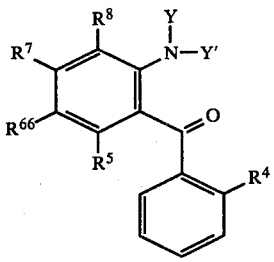

XXII wherein $R^{66}$ is nitro, lower dialkylamino, protected lower alkylamino or a group of the formula ZZ'N— and $R^4$, $R^5$, $R^7$, $R^8$, Y and Y' are as above,
whereby Y' can only be hydrogen when $R^{66}$ is a group of the formula ZZ'N—.

By removing the protecting group(s) denoted by Y' and/or Y from a compound of the above formula XXII without affecting other structural elements present in the molecule, there is obtained a benzophenone derivative of the formula

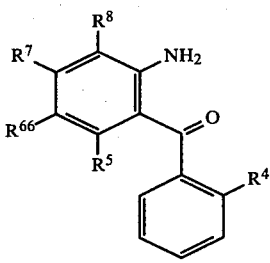

XXIII wherein $R^4$, $R^5$, $R^{66}$, $R^7$ and $R^8$ are as above.

Compounds of formula XXIII can then be converted, for example in analogy to the preparation of compounds of formula Xa from compounds of formula XI, into compounds of the formula

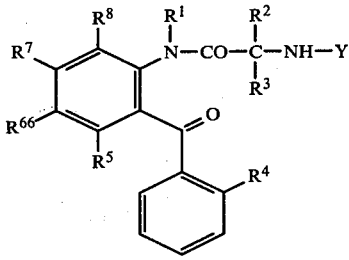

XXIV wherein $R^1$, $R^2$, $R^3$, $R^4$, $R^5$, $R^{66}$, $R^7$, $R^8$ and Y are as above.

By cleaving off the protecting group denoted by Y and, previously or in the same operation, also the protecting group(s) present in the group $R^{66}$ there are now obtained, from compounds of formula XXIV, compounds of formula II.

The compounds of formula III used as starting materials can be prepared for example, by selectively cleaving off the protecting group denoted by Y from compounds of formula XIV and from compounds of formula XXIV wherein $R^{66}$ is protected lower alkylamino or a group of the formula ZZ'N— and cyclising the resulting compound in analogy to embodiment (a) of the process.

Compounds of formula II can, however, also be prepared by reacting a compound of formula XXIII wherein $R^{66}$ is protected lower alkylamino or a group of the formula ZZ'N— with a dihalide of formula XII in analogy to embodiment (1) of the process, cyclising the product obtained in analogy to embodiment (a) of the process and treating a thus-obtained compound of the formula

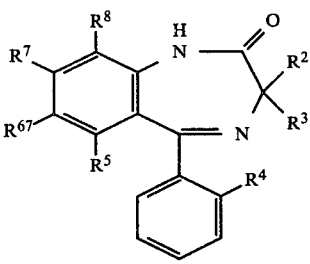

XXV wherein $R^{67}$ is protected lower alkylamino or a group of the formula ZZ'N— and $R^2$, $R^3$, $R^4$, $R^5$, $R^7$ and $R^8$ are as above.
with a suitable alkylating agent which yields the group $R^1$ [in analogy to embodiment (f) of the process].

A further possibility for the preparation of compounds of formula III comprises reacting a compound of formula Ia with a carbamoyl halide of formula XV or an isocyanate of formula XVI in analogy to embodiment (c) or (d) of the process or with a carboxylic acid halide of formula XVIII in analogy to embodiment (1) of the process, or reacting an isocyanate of formula VI, whose preparation is described below, with an amine of formula XIX in analogy to embodiment (e) of the process, or protecting the primary amino group in a compound of formula Ia and alkylating the protected compound obtained in analogy to embodiment (f) or (j) of the process depending on the nature of the protecting group used.

The compounds of formula VI used as starting materials can be prepared, as already mentioned above, from corresponding compounds of formula Ia by reaction with phosgene. In this case, conveniently a solution of phosgene in an organic solvent which is inert under the reaction conditions is prepared and then, while cooling, there is added thereto a solution of a compound of formula Ia, the mixture is thereupon heated to boiling under reflux for a short time, then cooled down and finally the solution obtained is made basic or at least neutral with a tertiary organic amino compound such as triethylamine. The resulting solution, containing a compound of formula VI, can be stored for several hours with the exclusion of moisture and in the cold; it is, as indicated above, used directly in the process of the invention without isolating the compound of formula VI contained therein.

The compounds of formula VIII used as starting materials are known or can be prepared according to methods known per se; for example, by cyclising a compound of formula XIII in analogy to embodiment (a) of the process and, if desired, reducing the nitro group in the resulting compound in analogy to embodiment (i) of the process to the amino group and dialkylating the latter in analogy to embodiment (j) of the process.

Compounds of formula VIII can, however, also be prepared by reacting a compound of formula XXIII wherein $R^{66}$ is lower dialkylamino as described earlier with a compound of formula XIII and cyclising the product obtained.

A further possibility for the preparation of compounds of formula VIII comprises removing, from a compound of formula XXV, the protecting group(s) present in the group $R^{67}$ and alkylating the resulting amino compound in analogy to embodiment (j) or (k) of the process.

The compounds of formulae, II, III and VI used as starting materials are novel and are likewise objects of the present invention.

Surprisingly, it has been shown that the 3,3-dialkyl-benzodiazepine derivatives of formula I hereinbefore display no or only very slight activities on the central nervous system, whereas they exhibit pronounced aldosterone-antagonistic properties. These aldosterone-antagonistic properties can be demonstrated in adrenalectomised rats as illustrated hereinafter.

If aldosterone is administered to adrenalectomised rats then there is observed, in comparison with untreated animals, a pronounced reduction of the sodium excretion (sodium retention), an increased potassium excretion (potassium excretion) as well as a reduction of the excreted urine volume. If compounds of formula I are administered to the animals before the treatment with aldosterone, then there is observed, in comparison with the animals which are treated only with aldosterone (control animals), a pronounced increase of the sodium excretion (i.e. the sodium retention caused by aldosterone is antagonised), whereas the potassium excretion and urine volume are influenced to a lesser extent.

The standard experiment is carried out as follows:

Female Holtzmann rats (150–180 g) are bilaterally adrenalectomised 70 to 74 hours before the beginning of the experiment. After the operation, the animals receive a customary rat dry feed and 0.9% sodium chloride solution for drinking. 16–17 hours before the beginning of the experiment the feed is removed from the animals, but they can subsequently drink, as before, 0.9% sodium chloride solution ad libitum. At the beginning of the experiment the substance to be tested as an aldosterone-antagonist is administered to the animals by means of a stomach probe. 30 minutes later the animals receive a subcutaneous injection of 4 mmg/kg of aldosterone. After a further 90 minutes, the urinary bladders of the animals are emptied by careful surprapubic pressure, whereupon the animals are placed individually in metabolic cages without food and without drink. The urine of the animals is then collected for 3 hours, whereupon their urinary bladders are once more emptied. The spontaneously excreted urine and the remaining urine obtained at the conclusion of the experiment by pressing-out the urinary bladders are collected in graduated centrifuge glasses. Sodium and potassium concentrations in the urine are determined with a flame photometer.

The following Table contains results obtained in the previously described experiment with representative compounds of formula I. In this Table there are given for each compound referred to therein the dosage administered (in mg/kg p.o.) as well as the percentage variation in the urine volume, the sodium excretion and the potassium excretion in comparison with the control animals (i.e. in comparison with the animals treated only with aldosterone). Moreover, the Table contains data relating to the acute toxicity of the compounds investigated (LD 50 in mg/kg in the case of single oral administration to mice).

TABLE

| | | | | | | | | | Toxicity and activity in the adrenalectomised rat | | | |
|---|---|---|---|---|---|---|---|---|---|---|---|---|
| $R^1$ | $R^2$ | $R^3$ | $R^4$ | $R^5$ | $R^7$ | $R^8$ | $R^6$ | | Dosage in mg/kg p.o. | Volume in % based on control animals | $[Na^\oplus]$ | $[K^\oplus]$ | LD 50 in mg/kg p.o. |
| —CH$_3$ | —CH$_3$ | —CH$_3$ | —F | —H | —H | —Cl | —NH$_2$ | 0,01 | 120 | 201 | 80 | >5000 |
| —CH$_3$ | —CH$_3$ | —CH$_3$ | —F | —Br | —Br | —H | —NH$_2$ | 1 | 161 | 281 | 76 | >5000 |
| —CH$_3$ | —CH$_3$ | —CH$_3$ | —Cl | —Br | —Br | —H | —NH$_2$ | 0,1 | 138 | 361 | 168 | >5000 |
| —CH$_3$ | —CH$_3$ | —CH$_3$ | —Cl | —Cl | —Cl | —H | —NH$_2$ | 0,1 | 98 | 215 | 85 | >5000 |
| —CH$_3$ | —CH$_3$ | —CH$_3$ | —F | —Cl | —H | —H | —NH$_2$ | 0,01 | 111 | 217 | 83 | >5000 |
| —CH$_3$ | —CH$_3$ | —CH$_3$ | —Cl | —H | —H | —H | —NHCONH(CH$_2$)$_2$OH | 0,1 | 131 | 309 | 76 | >5000 |
| —CH$_3$ | —CH$_3$ | —CH$_3$ | —F | —H | —H | —H | —NHCOC(CH$_3$)$_2$NH$_2$ | 0,1 | 101 | 246 | 102 | 1250–2500 |
| —CH$_3$ | —CH$_3$ | —CH$_3$ | —F | —Cl | —Cl | —Cl | —NH$_2$ | 1 | 124 | 208 | 108 | >5000 |
| —CH$_3$ | —CH$_3$ | —CH$_3$ | —F | —H | —Cl | —Cl | —NH$_2$ | 1 | 104 | 209 | 86 | — |
| —CH$_3$ | —CH$_3$ | —CH$_3$ | —Cl | —H | —H | —Cl | —NH$_2$ | 1 | 123 | 209 | 117 | >5000 |
| —CH$_3$ | —CH$_3$ | —CH$_3$ | —Cl | —Br | —H | —H | —NHCONH(CH$_2$)$_2$OH | 1 | 210 | 233 | 99 | >5000 |

The benzodiazepine derivatives of formula I and their pharmaceutically acceptable acid addition salts can be used as medicaments, for example, in the form of pharmaceutical preparations., The pharmaceutical preparations can be administered orally, for example in the form of tablets, coated tablets, dragées, hard and soft gelatin capsules, solutions, emulsions or suspensions. The administration can, however, also be carried out rectally (e.g. in the form of suppositories) or parenterally (e.g. in the form of injection solutions).

For the manufacture of tablets, coated tablets, dragées and hard gelatin capsules, the benzodiazepine derivatives of general formula I and their pharmaceutically acceptable acid addition salts can be processed with pharmaceutical inert, inorganic and/or organic carriers. Examples of carriers which can be used for tablets, dragées and hard gelatin capsules are lactose, maize starch or derivatives thereof, talc, stearic acid or its salts etc.

Suitable carriers for soft gelatin capsules are vegetable oils, waxes, fats, semi-solid and liquid polyols etc. Depending on the nature of the active substance no carriers are, however, generally necessary in the case of soft gelatin capsules.

Suitable carriers for the manufacture of solutions and syrups are, for example, water, polyols, saccharose, invert sugars, glucose and the like.

Suitable carriers for injection solutions are water, alcohols, polyols, glycerine, vegetable oils and the like.

Suitable carriers for suppositories are, for example, natural or hardened oils, waxes, fats, semi-liquid or liquid polyols and the like.

The pharmaceutical preparations can, moreover, contain other therapeutically valuable substances and/or adjuvants such as preserving agents, solubilising agents, stabilisers, wetting agents, emulsifiers, sweetening agents, colouring agents, flavouring agents, salts for varying the osmotic pressure, buffers, coating agents or antioxidants.

Medicaments containing one or more compounds of formula I or pharmaceutically acceptable acid addition salts thereof are likewise an object of the present invention as is a process for the manufacture of such medicaments, which is characterised by bringing one or more compounds of formula I or pharmaceutically acceptable acid addition salts thereof into galenical administration form. A further object of the present invention is the use of 3,3-dialkylbenzodiazepine derivatives of formula I and of pharmaceutically acceptable acid addition salts thereof in the control or prevention of illnesses, especially in the control or prevention of heart failure, of hepatic ascites, of primary aldosteronism and of idiophatic hypertension. The dosage can vary within wide limits and is, of course, fitted to the individual requirements in any particular case. In general, in the case of oral administration a daily dosage of about 20 mg to 1500 mg should be appropriate.

The following Examples illustrate the present invention, but are not intended to limit its extent. In these Examples all temperatures are given in degrees Centigrade.

EXAMPLE 1

(a) A solution of 206 g (2 mol) of α-aminoisobutyric acid in 1.2 l of absolute tetrahydrofuran is treated with 240 ml of thionyl chloride and stirred at room temperature for 24 hours. After the addition of 520 g of 2-amino-5-nitro-o'-fluorobenzophenone in 2 l of absolute tetrahydrofuran, the reaction mixture is stirred at room temperature for 3 days and concentrated to about two-thirds of the total volume. The precipitated hydrochloride is filtered off, treated with ice-water and methylene chloride and the aqueous phase is made alkaline with ammonia. Subsequently, the aqueous phase is extracted three times with methylene chloride containing 5% ethanol. After drying and evaporating the combined organic phases, there is obtained crude 2-amino-2'-(o-fluorobenzoyl)-2-methyl-4'-nitro-propionailide which is further processed directly. A sample of the material is recrystallised from methylene chloride/ether and melts at 154° C.

(b) A solution of 690 g (2 mol) of the above intermediate product in 3.6 l of toluene and 450 ml of glacial acetic acid is heated to boiling on a water-separator. After completion of the water-separation, the reaction mixture is concentrated and left to cool down. The crystallised-out product is filtered off, washed successively with toluene and ether and dried at room temperature in a water-jet vacuum. There is obtained 5(o-fluorophenyl)-1,3-dihydro-3,3-dimethyl-7-nitro-2H-1,4-benzodiazepin-2-one of melting point 243°–244°.

(c) 18.2 g (0.056 mol) of 5-(o-fluorophenyl)-1,3-dihydro-3,3-dimethyl-7-nitro-2H-1,4-benzodiazepin-2-one are dissolved in 150 ml of dry acetone, treated with 18 g of powdered potassium carbonate and 9 ml of methyl iodide and stirred at room temperature for 2½ hours. Subsequently, the reaction mixture is evaporated and the residue is partitioned between methylene chloride and water. After separating the organic phase, it is extracted several times more with methylene chloride. The combined organic extracts are then dried and evaporated. The residue is recrystallized from benzene/hexane/petroleum ether and gives 5-(o-fluorphenyl)-1,3-dihydro-1,3,3-trimethyl-7-nitro-2H-1,4-benzodiazepin-2-one of melting point 128°–129°.

EXAMPLE 2

1.5 g (0.0044 mol) of 5-(o-fluorophenyl)-1,3-dihydro-1,3,3-trimethyl-7-nitro-2H-1,4-benzodiazepin-2-one are dissolved in 15 ml of concentrated hydrochloric acid, treated with 3.3 g of tin (II) chloride and stirred at room temperature for 15 minutes. The reaction mixture is poured into a mixture of ice and soda solution and extracted with methylene chloride. After drying and evaporating the organic phase, the residue is recrystallised from ether. There is obtained 7-amino-5-(o-fluorophenyl)-1,3-dihydro-1,3,3-trimethyl-2H-1,4-benzodiazepin-2-one of melting point 190°–191°.

EXAMPLE 3

Chlorine gas is conducted slowly at between −5° and 0° through a solution of 6 g (0.019 mol) of 7-amino-5-(o-fluorophenyl)-1,3-dihydro-1,3,3-trimethyl-2H-1,4-benzodiazepin-2-one in 70 ml of concentrated hydrochloric acid until the starting material has almost completely been consumed. The reaction mixture is poured into a mixture of ice and soda solution, whereupon it is extracted with methylene chloride and the extract is dried and evaporated. The residue is chromatographed on 300 g of silica gel with methylene chloride/ethyl acetate (10:1) as the elution agent. From ether-petroleum ether there is obtained 7-amino-6-chloro-5-(o-fluorophenyl)-1,3-dihydro-1,3,3-trimethyl-2H-1,4-benzodiazepin-2-one of melting point 192°–193°.

EXAMPLE 4

(a) A solution of 3.5 g (0.01 mol) of 7-amino-6-chloro-5-(o-fluorophenyl)-1,3-dihydro-1,3,3-trimethyl-2H-1,4-benzodiazepin-2-one in 60 ml of 1,2-dichloroethane is added dropwise while stirring to a solution of 1.5 g (0.015 mol) of phosgene in ice-cooled 1,2-dichloroethane so that the reaction temperature does not exceed 10°. Subsequently, the reaction mixture is heated at reflux while stirring for a further 10 minutes, whereupon it is cooled to ca 10° and made basic with triethylamine. There is thus obtained a solution of [6-chloro-5-(o-fluorophenyl)-2,3-dihydro-1,3,3-trimethyl-2-oxo-1H-1,4-benzodiazepin-7-yl]isocyanate which can be stored in the cold for several hours with the exclusion of moisture. It is further processed without isolation of the isocyanate contained therein.

(b) The above-obtained solution of the isocyanate is added to 2 ml of ethanolamine in 1,2-dichloroethane and the reaction mixture is evaporated. The residue is purified on 150 g of silica gel with methylene chloride, methylene chloride/ethyl acetate (1:1) and ethyl acetate as the elution agent. From acetone/ether there is obtained 1-[6-chloro-5-(o-fluorophenyl)-2,3-dihydro-1,3,3-trimethyl-2-oxo-1H-1,4-benzodiazepin-7-yl]-3-(2-hydroxyethyl)urea of melting point 146°–147° (decomposition).

EXAMPLE 5

6.6 g (0.021 mol) of 7-amino-5-(o-fluorophenyl)-1,3-dihydro-1,3,3-trimethyl-2H-1,4-benzodiazepin-2-one, dissolved in 50 ml of concentrated aqueous hydrobromic acid, are treated slowly at between 0° and 5° with 1.2 l of bromine and stirred at 0° for 1 hour. Subsequently, the reaction mixture is poured into a mixture of ice and soda solution, extracted with methylene chloride and the organic extract is evaporated. The residue is purified on 300 g of silica gel with methylene chloride/ethyl acetate (20:1). From ethyl acetate/ether there is obtained 7-amino-6-bromo-5-(o-fluorophenyl)-1,3-dihydro-1,3,3-trimethyl-2H-1,4-benzodiazepin-2-one of melting point 217°–220°.

EXAMPLE 6

From 2.1 g (0.0054 mol) of 7-amino-6-bromo-5-(o-fluorophenyl)-1,3-dihydro-1,3,3-trimethyl-2H-1,4-benzodiazepin-2-one there is obtained, in analogy to the details in Example 4,1-[6-bromo-5-(o-fluorophenyl)-2,3-dihydro-1,3,3-trimethyl-2-oxo-1H-1,4-benzodiazepin-7-yl]-3-(2-hydroxyethyl)urea of melting point 202° (ethanol/ethyl acetate/n-hexane).

EXAMPLE 7

(a) From 70 g (0.25 mol) of 2-amino-5-nitro-2'-chlorobenzophenone there is obtained, in analogy to the details in paragraph (a) of Example 1, 2-amino-2'-(o-chlorobenzoyl)-2-methyl-4'-nitro-propionanilide of melting point 138°–139° (ether/petroleum ether).

(b) From 76 g (0.21 mol) of 2-amino-2'-(o-chlorobenzoyl)-2-methyl-4'-nitro-propionanilide there is obtained, in analogy to the details in paragraph (b) of Example 1, 5-(o-chlorophenyl)-1,3-dihydro-3,3-dimethyl-7-nitro-2H-1,4-benzodiazepin-2-one of melting point 242° (methylene chloride/n-hexane).

(c) From 59 g (0.17 mol) of 5-(o-chlorophenyl)-1,3-dihydro-3,3-dimethyl-7-nitro-2H-1,4-benzodiazepin-2-one there is obtained, in analogy to the details in paragraph (c) of Example 1, 5-(o-chlorophenyl)-1,3-dihydro-1,3,3-trimethyl-7-nitro-2H-1,4-benzodiazepin-2-one of melting point 125°–127° (methylene chloride/ethyl acetate).

EXAMPLE 8

From 44.5 g (0.124 mol) of 5-(o-chlorophenyl)-1,3-dihydro-1,3,3-trimethyl-7-nitro-2H-1,4-benzodiazepin-2-one there is obtained, in analogy to the details in Example 2, 7-amino-5-(o-chlorophenyl)-1,3-dihydro-1,3,3-trimethyl-2H-1,4-benzodiazepin-2-one of melting point 177°–178° (ether/n-hexane).

EXAMPLE 9

From 8 g (0.024 ml) of 7-amino-5-(o-chlorophenyl)-1,3-dihydro-1,3,3-trimethyl-2H-1,4-benzodiazepin-2-one there is obtained, in analogy to the details in Example 4, via [5-(o-chlorophenyl)-2,3-dihydro-1,3,3-trimethyl-2-oxo-1H-1,4-benzodiazepin-7-yl]isocyanate, 1-[5-(o-chlorophenyl)-2,3-dihydro-1,3,3-trimethyl-2-oxo-1H-1,4-benzodiazepin-7-yl]-3-(2-hydroxyethyl)urea of melting point 85°–110° (ethyl acetate/n-hexane).

EXAMPLE 10

17 g (0.052 mol) of 7-amino-5-(o-chlorophenyl)-1,3-dihydro-1,3,3-trimethyl-2H-1,4-benzodiazepin-2-one in 100 ml of glacial acetic acid are treated slowly with a solution of 4 g of chlorine gas in 50 ml of glacial acetic acid. The reaction mixture is stirred at room temperature, evaporated after 60 minutes and the residue is treated with aqueous ammonia and methylene chloride. After extracting the aqueous phase with methylene chloride, the organic extract is dried and evaporated. The crude product is purified by chromatography on 600 g of silica gel with methylene chloride and methylene chloride/ethyl acetate (5:1) as the elution agent. From ethyl acetate/ether/n-hexane there is obtained 7-amino-6-chloro-5-(o-chlorophenyl)-1,3-dihydro-1,3,3-trimethyl-2H-1,4-benzodiazepin-2-one of melting point 195°–196°.

EXAMPLE 11

16 g (0.049 mol) of 7-amino-5-(o-chlorophenyl)-1,3-dihydro-1,3,3-trimethyl-2H-1,4-benzodiazepin-2-one in 160 ml of glacial acetic acid are treated slowly while stirring with 8.5 g of bromine in 10 ml of glacial acetic acid. After 60 minutes at room temperature, the reaction mixture is concentrated and the residue is partitioned between aqueous ammonia and methylene chloride. The aqueous phase is extracted several times more with methylene chloride. The combined organic extracts are dried and evaporated. The crude product is purified on 500 g of silica gel with methylene chloride/ethyl acetate (5:1) as the elution agent. From ethyl acetate/ether there is obtained 7-amino-6-bromo-5-(o-chlorophenyl)-1,3-dihydro-1,3,3-trimethyl-2H-1,4-benzodiazepin-2-one of melting point 188°–189°.

EXAMPLE 12

From 4.5 g (0.011 mol) of 7-amino-6-bromo-5-(o-chlorophenyl)-1,3-dihydro-1,3,3-trimethyl-2H-1,4-benzodiazepin-2-one there is obtained, in analogy to the details in Example 4, via [6-bromo-5-(o-chlorophenyl)-2,3-dihydro-1,3,3-trimethyl-2-oxo-1H-1,4-benzodiazepin-7-yl]isocyanate, 1-[6-bromo-5-(o-chlorophenyl)-2,3-dihydro-1,3,3-trimethyl-2-oxo-1H-1,4-benzodiazepin-7yl]-3-(2-hydroxyethyl)urea of melting point 214°–218° (acetone/ether).

EXAMPLE 13

(a) A solution of 160 g (0.49 mol) of 5-(o-fluorophenyl)-1,3-dihydro-3,3-dimethyl-7-nitro-2H-1,4-benzodiazepin-2-one in 400 ml of concentrated hydrochloric acid and 400 ml of formic acid is treated while stirring with a solution of 46 g of chlorine gas in 400 ml of 1,2-dichloroethane. The reaction mixture, which consists of two phases, is stirred at room temperature, whereby after 3 days a further 25 g of chlorine gas in 200 ml of 1,2-dichloroethane are added and after 5 days a further 5 g of chlorine gas in 40 ml of 1,2-dichloroethane are added. After 7 days, the mixture is concentrated, treated with ice-water, made alkaline with aqueous ammonia and extracted four times with methylene chloride. The organic extract is concentrated and treated with 600 ml of isopropanol. Subsequently, the residual methylene chloride is removed on a steam-bath and the product is left to crystallise. There is obtained 9-chloro-5-(o-fluorophenyl)-1,3-dihydro-3,3-dimethyl-7-nitro-2H-1,4-benzodiazepin-2-one of melting point 174°–175°.

(b) From 120 g (0.33 mol) of 9-chloro-5-(o-fluorophenyl)-1,3-dihydro-3,3-dimethyl-7-nitro-2H-1,4-benzodiazepin-2-one there is obtained, in analogy to the details in paragraph (c) of Example 1, 9-chloro-5-(o-fluorophenyl)-1,3-dihydro-1,3,3-trimethyl-7-nitro-2H-1,4-benzodiazepin-2-one of melting point 146°–147° (isopropanol/methylene chloride).

EXAMPLE 14

From 24 g (0.064 ml) of 9-chloro-5-(o-fluorophenyl)-1,3-dihydro-1,3,3-trimethyl-7-nitro-2H-1,4-benzodiazepin-2-one there is obtained, in analogy to the details in Example 2, 7-amino-9-chloro-5-(o-fluorophenyl)-1,3-dihydro-1,3,3-trimethyl-2H-1,4-benzodiazepin-2-one of melting point 237°–238° (isopropanol).

EXAMPLE 15

From 5.1 g (0.015 mol) of 7-amino-5-(o-chlorophenyl)-1,3-dihydro-1,3,3-trimethyl-2H-1,4-benzodiazepin-2-one and pyrrolidone there is obtained, in analogy to the details in Example 4, via [5-(o-chlorophenyl)-2,3-dihydro-1,3,3-trimethyl-2-oxo-1H-1,4-benzodiazepin-7-yl]isocyanate, N-[5-(o-chlorophenyl)-2,3-dihydro-1,3,3-trimethyl-2-oxo-1H-1,4-benzodiazepin-7-yl]-1-pyrrolidinecarboxamide of melting point 248°–150° (ethyl acetate/ether).

EXAMPLE 16

From 25 g (0.073 mol) of 5-(o-chlorophenyl)-1,3-dihydro-3,3-dimethyl-7-nitro-2H-1,4-benzodiazepin-2-one and isopropyl bromide there is obtained, in analogy to the details in paragraph (c) of Example 1, but with a reaction period of 7 days, 5-(o-chlorophenyl)-1,3-dihydro-1-isopropyl-3,3-dimethyl-7-nitro-2H-1,4-benzodiazepin-2-one of melting point 197°–198° (ether/n-hexane).

EXAMPLE 17

From 1.7 g (0.005 mol) of 5-(o-chlorophenyl)-1,3-dihydro-3,3-dimethyl-7-nitro-2H-1,4-benzodiazepin-2-one and ethyl bromide there is obtained, in analogy to the details in paragraph (c) of Example 1, with a reaction period of 36 hours, 5-(o-chlorophenyl)-1-ethyl-1,3-dihydro-3,3-dimethyl-7-nitro-2H-1,4-benzodiazepin-2-one of melting point 174° (ether).

EXAMPLE 18

From 25 g (0.067 mol) of 5-(o-chlorophenyl)-1-ethyl-1,3-dihydro-3,3-dimethyl-7-nitro-2H-1,4-benzodiazepin-2-one there is obtained, in analogy to the details in Example 2, 7-amino-5-(o-chlorophenyl)-1-ethyl-1,3-dihydro-3,3-dimethyl-2H-1,4-benzodiazepin-2-one of melting point 178° (ether).

EXAMPLE 19

From 25 g (0.073 mol) of 5-(o-chlorophenyl)-1,3-dihydro-3,3-dimethyl-7-nitro-2H-1,4-benzodiazepin-2-one and n-butyl bromide there is obtained, in analogy to the details in paragraph (c) of Example 1, with a reaction period of 4 days, 1-butyl-5-(o-chlorophenyl)-1,3-dihydro-3,3-dimethyl-7-nitro-2H-1,4-benzodiazepin-2-one of melting point 129° (ether/n-hexane).

EXAMPLE 20

From 25 g (0.073 mol) of 5-(o-chlorophenyl)-1,3-dihydro-3,3-dimethyl-7-nitro-2H-1,4-benzodiazepin-2-one and 2-bromoethanol there is obtained, in analogy to the details in paragraph (c) of Example 1, with a reaction period of 7 days, 5-(o-chlorophenyl)-1,3-dihydro-1-(2-hydroxyethyl)-3,3-dimethyl-7-nitro-2H-1,4-benzodiazepin-2-one of melting point 124°–125° (ether/n-hexane).

EXAMPLE 21

From 25 g (0.073 mol) of 5-(o-chlorophenyl)-1,3-dihydro-3,3-dimethyl-7-nitro-2H-1,4-benzodiazepin-2-one and 2-diethylaminoethyl chloride there is obtained, in analogy to the details in paragraph (c) of Example 1, with a reaction period of 60 hours, 5-(o-chlorophenyl)-1,3-dihyro-1-(2-diethylaminoethyl)-3,3-dimethyl-7-nitro-2H-1,4-benzodiazepin-2-one of melting point 109° (ether/n-hexane).

EXAMPLE 22

From 12.5 g (0.032 mol) of 5-(o-chlorophenyl)-1,3-dihydro-1-(2-hydroxyethyl)-3,3-dimethyl-7-nitro-2H-1,4-benzodiazepin-2-one there is obtained, in analogy to the details in Example 2, 7-amino-5-(o-chlorophenyl)-1,3-dihydro-1-(2-hydroxyethyl)-3,3-dimethyl-2H-1,4-benzodiazepin-2-one of melting point 192°–194° (ethyl acetate/ether).

EXAMPLE 23

From 6.5 g (0.018 mol) of 7-amino-5-(o-chlorophenyl)-1,3-dihydro-1-(2-hydroxyethyl)-3,3-dimethyl-2H-1,4-benzodiazepin-2-one there is obtained, in analogy to the details in paragraph (b) of Example 4, via [5-(o-chlorophenyl)-2,3-dihydro-1-(2-hydroxyethyl)-3,3-dimethyl-2-oxo-1H-1,4-benzodiazepin-7-yl]isocyanate, 1,-[5-o-chlorophenyl)-2,3-dihydro-1-(2-hydroxyethyl)-3,3-dimethyl-2-oxo-1H-1,4-benzodiazepin-7-yl]-3-(2-hydroxyethyl)urea of melting point 175°–176° (ethanol/ethyl acetate).

EXAMPLE 24

From 10 g (0.022 mol) of 5-(o-chlorophenyl)-1-(2-diethylaminoethyl)-1,3-dihydro-3,3-dimethyl-7-nitro-2H-1,4-benzodiazepin-2-one there is obtained, in analogy to the details in Example 2, 7-amino-5-(o-chlorophenyl)-1-(2-diethylaminoethyl)-1,3-dihydro-3,3-dimethyl-2H-1,4-benzodiazepin-2-one of melting point 70° (ethanol/water).

EXAMPLE 25

From 7.5 g (0.019 mol) of 5-(o-chlorophenyl)-1,3-dihydro-1-isopropyl-3,3-dimethyl-7-nitro-2H-1,4-benzodiazepin-2-one there is obtained, in analogy to the details in Example 2, 7-amino-5-(o-chlorophenyl)-1,3-dihydro-1-isopropyl-3,3-dimethyl-2H-1,4-benzodiazepine of melting point 169°–170° (ether/n-hexane).

EXAMPLE 26

From 4 g (0.011 mol) of 7-amino-5-(o-chlorophenyl)-1,3-dihydro-1-isopropyl-3,3-dimethyl-2H-1,4-benzodiazepin-2-one there is obtained, in analogy to the details in Example 4, via [5-(o-chlorophenyl)-2,3-dihydro-1-isopropyl-3,3-dimethyl-2-oxo-1H-1,4-benzodiazepin-7yl]isocyanate, 1-[5-(o-chlorophenyl)2,3-dihydro-1-isopropyl-3,3-dimethyl-2-oxo-1H-1,4-benzodiazepin-7-yl]-3-(2-hydroxyethyl)urea of melting point 243°–244° (1,2-dichloroethane/methylene chloride).

EXAMPLE 27

8 g (0.026 mol) of 7-amino-5-(o-fluorophenyl)-1,3-dihydro-1,3,3-trimethyl-2H-1,4-benzodiazepin-2-one are stirred at room temperature for 1 hour with 5 g of α-aminoisobutyric acid chloride hydrochloride in 30 ml of tetrahydrofuran, 8 g of potassium carbonate are subsequently added thereto and, after a further 15 minutes, the mixture is treated with methylene chloride and water. The organic phase is separated and the aqueous phase is extracted four times with methylene chloride. The combined organic extracts are dried and evaporated. The residue is purified on 350 g of silica gel with methylene chloride/ethyl acetate (1:1) and ethyl acetate as the elution agent. From ethyl acetate/ether there is obtained 2-amino-N-[5-(o-fluorophenyl)-2,3-dihydro- 1,3,3-trimethyl-2-oxo-1H-1,4-benzodiazepin-7-yl]-2-methylpropionamide of melting point 250°.

EXAMPLE 28

2 g (0.005 mol) of 2 amino-N-[5-(o-fluorophenyl)-2,3-dihydro-1,3,3-trimethyl-2-oxo-1H-1,4-benzodiazepin-7-yl]-2-methylpropionamide are dissolved in 50 ml of 1,2-dichloroethane and added to 1 g of phosgene in 50 ml of 1,2-dichloroethane at room temperature. The reaction mixture is stirred for ½ hour and subsequently made basic with triethylamine. The mixture is treated with water and extracted with methylene chloride. The organic phase is dried and evaporated. The residue gives, from ethyl acetate/ether, 3-[5-(o-fluorophenyl)-2,3-dihydro-1,3,3-trimethyl-2-oxo-1H-1,4-benzodiazepin-7-yl]-5,5-dimethylhydantoin of melting point 286°–287°.

EXAMPLE 29

From 10 g (0.028 mol) of 9-chloro-5-(o-fluorophenyl)-1,3-dihydro-3,3-dimethyl-7-nitro-2H-1,4-benzodiazepin-2-one and n-butyl bromide there is obtained, in analogy to the details in paragraph (c) of Example 1, with a reaction period of 9 days and purification of the product by chromatography on silica gel (elution agent: methylene chloride), 1-butyl-9-chloro-5-(o-fluorophenyl)-1,3-dihydro-3,3-dimethyl-7-nitro-2H-1,4-benzodiazepin-2-one of melting point 125°–127° (hexane/petroleum ether).

EXAMPLE 30

4.75 g (0.014 mol) of 7-amino-9-chloro-5-(o-fluorophenyl)-1,3-dihydro-1,3,3-trimethyl-2H-1,4-benzodiazepin-2-one are dissolved in 100 ml of dry methylene chloride and treated with 4.2 g of N-chlorosuccinamide. The reaction mixture is heated at reflux for 40 hours, treated with 25 percent aqueous ammonia and extracted several times with methylene chloride. After drying and evaporating the organic phase, the residue is chromatographed on 250 g of silica gel with methylene chloride/ethyl acetate (20:1) as the elution agent. There is obtained 7-amino-6,8,9-trichloro-1,3-dihydro-5-(o-fluorophenyl)-1,3,3-trimethyl-2H-1,4-benzodiazepin-2-one of melting point 165°–166° (ether/n-hexane).

EXAMPLE 31

From 4.75 g (0.014 mol) of 7-amino-9-chloro-5-(o-fluorophenyl)-1,3-dihydro-1,3,3-trimethyl-2H-1,4-benzodiazepin-2-one and 2.1 g (0.0016 mol) of N-chlorosuccinimide there is obtained, in analogy to the details in Example 30, 7-amino-6,9-dichloro-5-(o-fluorophenyl)-1,3-dihydro-1,3,3-trimethyl-2H-1,4-benzodiazepin-2-one of melting point 190°–192° (ether/n-hexane).

EXAMPLE 32

From 4.75 g (0.014 mol) of 7-amino-9-chloro-5-(o-fluorophenyl)-1,3-dihydro-1,3,3-trimethyl-2H-1,4-benzodiazepin-2-one there is obtained, in analogy to the details in Example 30, 7-amino-8,9-dichloro-5-(o-fluorophenyl)-1,3-dihydro-1,3,3-trimethyl-2H-1,4-benzodiazepin-2-one of melting point 169°–172° (ether).

EXAMPLE 33

From 10 g (0.028 mol) of 9-chloro-5-(o-fluorophenyl)-1,3-dihydro-3,3-dimethyl-7-nitro-2H-1,4-benzodiazepin-2-one and ethyl bromide there is obtained, in analogy to the details in paragraph (c) of Example 1, with a reaction period of 8 days and chromatography of the crude product on silica gel (elution agent: methylene chloride), 9-chloro-1-ethyl-5-(o-fluorophenyl)-1,3-dihydro-3,3-dimethyl-7-nitro-2H-1,4-benzodiazepin-2-one of melting point 117°–120° (ether/n-hexane).

EXAMPLE 34

From 3.8 g (0.01 mol) of 9-chloro-1-ethyl-5-(o-fluorophenyl)-1,3-dihydro-3,3-dimethyl-7-nitro-2H-1,4-benzodiazepin-2-one there is obtained, in analogy to the details in Example 2, 7-amino-9-chloro-1-ethyl-5-(o-fluorophenyl)-1,3-dihydro-3,3-dimethyl-2H-1,4-benzodiazepin-2-one of melting point 156° (ether/n-hexane).

EXAMPLE 35

(a) From 10 g (0.029 mol) of 5-(o-chlorophenyl)-1,3-dihydro-3,3-dimethyl-7-nitro-2H-1,4-benzodiazepin-2-one there is obtained, in analogy to the details in paragraph (a) of Example 13, 9-chloro-5-(o-chlorophenyl)-1,3-dihydro-3,3-dimethyl-7-nitro-2H-1,4-benzodiazepin-2-one of melting point 105° (ether/n-hexane).

(b) From 3.1 g (0.0082 mol) of 9-chloro-5-(o-chlorophenyl)-1,3-dihydro-3,3-dimethyl-7-nitro-2H-1,4-benzodiazepin-2-one there is obtained, in analogy to the details in paragraph (c) of Example 1, 9-chloro-5-(o-chlorophenyl)-1,3-dihydro-1,3,3-trimethyl-7-nitro-2H-1,4-benzodiazepin-2-one of melting point 121° (ether/n-hexane).

EXAMPLE 36

From 2.2 g (0.0056 mol) of 9-chloro-5-(o-chlorophenyl)-1,3-dihydro-1,3,3-trimethyl-7-nitro-2H-1,4-benzodiazepin-2-one there is obtained, in analogy to the details in Example 2, 7-amino-9-chloro-5-(o-chlorophenyl)-1,3-dihydro-1,3,3-trimethyl-2H-1,4-benzodiazepin-2-one of melting point 254° (ether/n-hexane).

EXAMPLE 37

From 4.5 g (0.011 mol) of 1-butyl-9-chloro-5-(o-fluorophenyl)-1,3-dihydro-3,3-dimethyl-7-nitro-2H-1,4-benzodiazepin-2-one there is obtained, in analogy to the details in Example 2, 7-amino-1-butyl-9-chloro-5-(o-fluorophenyl)-1,3-dihydro-3,3-dimethyl-2H-1,4-benzodiazepin-2-one of melting point 151° (ether/n-hexane).

EXAMPLE 38

346 mg (1 mmol) of 7-amino-9-chloro-5-(o-fluorophenyl-1,3-dihydro-1,3,3-trimethyl-2H-1,4-benzodiazepin-2-one are heated at reflux for 1 hour in 4 ml of formic acid and 4 ml of formalin solution. The reaction mixture is treated with ice, aqueous ammonia and methylene chloride, and extracted several times with methylene chloride. After drying and evaporating the organic phase, the residue is chromatographed on 10 g of silica gel (particle size 0.04–0.06 mm) under pressure (0.2–0.4 atmospheres of nitrogen) with methylene chloride as the elution agent. There is obtained 9-chloro-7-(dimethylamino)-5-(o-fluorophenyl)-1,3-dihydro-1,3,3-trimethyl-2H-1,4-benzodiazepin-2-one of melting point 227° (ether/petroleum ether).

EXAMPLE 39

12 g (0.035 mol) of 7-amino-9-chloro-5-(o-fluorophenyl)-1,3-dihydro-1,3,3-trimethyl-2H-1,4-benzodiazepin-2-one are dissolved in 360 ml of dry tetrahydrofuran, treated with 10 g of ground sodium bicarbonate and 8 ml of chloroformic acid benzyl ester and stirred at room temperature for 3½ hours. The mixture is treated with ethyl acetate and water, and separated aqueous phase is extracted twice with ethyl acetate and the combined organic extracts are dried and evaporated. The residue is chromatographed on 600 g of silica gel with methylene chloride/ethyl acetate (20:1) as the elution agent. From ether there is obtained benzyl 9-chloro-5-(o-fluorophenyl)-2,3-dihydro-1,3,3-trimethyl-2-oxo-1H-1,4-benzodiazepine-7-carbamate of melting point 212°.

(b) 9.6 g (0.02 mol) of benzyl 9-chloro-5-(o-fluorophenyl)-2,3-dihydro-1,3,3-trimethyl-2-oxo-1H-1,4-benzodiazepine-7-carbamate in 50 ml of t-butanol are treated with 3 g of potassium t-butanolate and stirred at 40° for ½ hour. After adding 3.5 ml of n-butyl iodide, the mixture is stirred at room temperature for 28 days, treated with methylene chloride and 10 percent sodium bicarbonate solution and the separated aqueous phase is extracted twice more with methylene chloride. The combined organic extracts are dried and evaporated. The residue is chromatographed on 300 g of silica gel (particle size 0.04–0.06 mm) under pressure (0.2–0.4 atmospheres of nitrogen) with methylene chloride/ethyl acetate (20:1) as the elution agent. The thus-obtained benzyl N-butyl-9-chloro-5-(o-fluorophenyl)-2,3-dihydro-1,3,3-trimethyl-2-oxo-1H-1,4-benzodiazepine-7-carbamate is further processed directly.

(c) 6 g of the above product in 80 ml of dry ethanol are stirred at room temperature with 500 mg of 5 percent palladium/carbon and hydrogen, with a soda lime cartridge (in order to eliminate carbon dioxide). After 6 hours, the catalyst is filtered off and the filtrate is concentrated. The residue is chromatographed on 200 g of silica gel (particle size 0.04–0.06 mm) under pressure (0.2–0.4 atmospheres of nitrogen) with methylene chloride/ethyl acetate (10:1) as the elution agent. There is obtained 7-(butylamino)-9-chloro-5-(o-fluorophenyl)-1,3-dihydro-1,3,3-trimethyl-2H-1,4-benzodiazepin-2-one of melting point 113°–115° (hexane).

EXAMPLE 40

(a) From 9.6 g (0.02 mol) of benzyl 9-chloro-5-(o-fluorophenyl)-2,3-dihydro-1,3,3-trimethyl-2-oxo-1H-1,4-benzodiazepine-7-carbamate there is obtained, in analogy to the details in paragraph (b) of Example 39, benzyl 9-chloro-N-ethyl-5-(o-fluorophenyl)-2,3-dihydro-1,3,3-trimethyl-2-oxo-1H-1,4-benzodiazepine-7-carbamate of melting point 125°–127° (hexane).

(b) From 9.6 g (0.019 mol) of benzyl 9-chloro-N-ethyl-5-(o-fluorophenyl)-2,3-dihydro-1,3,3-trimethyl-2-oxo-1H-1,4-benzodiazepine-7-carbamate there is obtained, in analogy to the details in paragraph (c) of Examples 39, 9-chloro-7-(ethylamino)-5-(o-fluorophenyl)-1,3-dihydro-1,3,3-trimethyl-2H-1,4-benzodiazepin-2-one of melting point 150°–151° (ether/petroleum ether).

EXAMPLE 41

(a) 30 g (0.092 mol) of 5-(o-fluorophenyl)-1,3-dihydro-3,3-dimethyl-7-nitro-2H-1,4-benzodiazepin-2-one are dissolved in 600 ml of concentrated hydrochloric acid and 600 ml of formic acid, treated with 49.5 g of N-bromosuccinimide and stirred at room temperature for 48 hours. Subsequently, an additional 33 g of N-bromosuccinimide are added thereto and the mixture is stirred at room temperature for 4 days. The solution is evaporated and the residue is poured into ice and aqueous ammonia. After extracting the aqueous solution three times with methylene chloride, the organic phase is dried and evaporated. The residue is chromatographed on 2 kg of silica gel with methylene chloride and methylene chloride/ethyl acetate (20:1) as the elution agent. There is obtained 9-bromo-5-(o-fluorophenyl)-1,3-dihydro-3,3-dimethyl-7-nitro-2H-1,4-benzodiazepin-2-one of melting point 164° (ether/n-hexane).

(b) From 21.8 g (0.054 mol) of 9-bromo-5-(o-fluorophenyl)-1,3-dihydro-3,3-dimethyl-7-nitro-2H-1,4-benzodiazepin-2-one there is obtained, in analogy to the details in paragraph (c) of Example 1, 9-bromo-5-(o-fluorophenyl)-1,3-dihydro-1,3,3-trimethyl-7-nitro-2H-1,4-benzodiazepin-2-one of melting point 180° (ether/petroleum ether).

EXAMPLE 42

From 16 g (0.038 mol) of 9-bromo-5-(o-fluorophenyl)-1,3-dihydro-1,3,3-trimethyl-7-nitro-2H-1,4-benzodiazepin-2-one there is obtained, in analogy to the details in Example 2, 7-amino-9-bromo-5-(o-fluorophenyl)-1,3-dihydro-1,3,3-trimethyl-2H-1,4-benzodiazepin-2-one of melting point 228° (methylene chloride/petroleum ether).

EXAMPLE 43

From 32 g (0.088 mol) of 9-chloro-5-(o-fluorophenyl)-1,3-dihydro-3,3-dimethyl-7-nitro-2H-1,4-benzodiazepin-2-one and propyl bromide there is obtained, in analogy to the details in paragraph (c) of Example 1, with a reaction period of 3 days, 9-chloro-5-(o-fluorophenyl)-1,3-dihydro-3,3-dimethyl-7-nitro-1-propyl-2H-1,4-benzodiazepin-2-one of melting point 142°–143° (ether/n-hexane).

EXAMPLE 44

From 15 g (0.037 mol) of 9-chloro-5-(o-fluorophenyl)-1,3-dihydro-3,3-dimethyl-7-nitro-1-propyl-2H-1,4-benzodiazepin-2-one there is obtained, in analogy to the details in Example 2, 7-amino-9-chloro-5-(o-fluorophenyl)-1,3-dihydro-3,3-dimethyl-1-propyl-2H-1,4-benzodiazepin-2-one of melting point 178°–179° (ethyl acetate/ether/n-hexane).

EXAMPLE 45

A solution of 21.5 g (0.0691 mol) of 7-amino-5-(o-fluorophenyl)-1,3-dihydro-1,3,3-trimethyl-2H-1,4-benzodiazepin-2-one and 25.8 g (0.145 mol) of N-bromosuccinimide in 400 mol of methylene chloride is stirred at room temperature for 78 hours under argon and subsequently poured into 500 ml of 2 N sodium carbonate solution. The organic phase is separated and the aqueous phase is extracted again with methylene chloride. The combined organic extracts are washed with water, dried and evaporated. The residue is chromatographed on 500 g of silica gel with chloroform as the elution agent. There is obtained 7-amino-6,8-dibromo-5-(o-fluorophenyl)-1,3-dihydro-1,3,3-trimethyl-2H-1,4-benzodiazepin-2-one of melting point 202°.

EXAMPLE 46

From 20 g (0.061 mol) of 7-amino-5-(o-chlorophenyl)-1,3-dihydro-1,3,3-trimethyl-2H-1,4-benzodiazepin-2-one there is obtained, in analogy to the details of Example 45, 7-amino-6,8-dibromo-5-(o-chlorophenyl)-1,3-dihydro-1,3,3-trimethyl-2H-1,4-benzodiazepin-2-one of melting point 110° (methylene chloride/cyclohexane).

EXAMPLE 47

From 20 g (0.0642 mol) of 7-amino-5-(o-fluorophenyl)-1,3-dihydro-1,3,3-trimethyl-2H-1,4-benzodiazepin-2-one and 18 g (0.134 mol) of N-chlorosuccinimide there is obtained, in analogy to the details in Example 45, 7-amino-6,8-dichloro-5-(o-fluorophenyl)-1,3-dihydro-1,3,3-trimethyl-2H,-1,4-benzodiazepin-2-one of melting point 208° (methylene chloride/cyclohexane).

EXAMPLE 48

From 20 g (0.061 mol) of 7-amino-5-(o-chlorophenyl)-1,3-dihydro-1,3,3-trimethyl-2H-1,4-benzodiazepin-2-one there is obtained, in analogy to the details in Example 45, 7-amino-6,8-dichloro-5-(o-chlorophenyl)-1,3-dihydro-1,3,3-trimethyl-2H-1,4-benzodiazepin-2-one of melting point 105° (methylene chloride/cyclohexane).

EXAMPLE 49

(a) A mixture of 5 g (0.014 mol) of 2-amino-2'-(o-fluorophenyl)-2-methyl-4'-nitro-propionanilide, 4 g of powdered potassium carbonate and 2.5 ml of chloroformic acid benzyl ester in 40 ml of tetrahydrofuran is stirred at room temperature overnight and, after filtering off the potassium carbonate, the filtrate is concentrated. The residue is chromatographed on a pressure column containing 250 g of silica gel (particle size 0.04–0.06 mm) under 0.2–0.4 atmospheres of nitrogen with methylene chloride as the elution agent. There is obtained benzyl [1-[[2-(o-fluorobenzoyl)-4-nitrophenyl]carbamoyl]-1-methyl-ethyl]-carbamate of melting point 153°–155° (n-hexane).

(b) A solution of 500 mg of benzyl [1-[[2-(o-fluorobenzoyl)-4-nitrophenyl]-carbamoyl]-1-methyl-ethyl]carbamate (1.043 mol) and 150 mg of potassium t-butanolate in 20 ml of t-butanol is treated with 0.15 ml of methyl iodide and stirred at room temperature for 2.5 days. The reaction mixture is buffered with glacial acetic acid and concentrated. The residue is partitioned between methylene chloride and 10 percent aqueous sodium bicarbonate solution. After drying the organic phase overnight and concentrating, the residue is chromatographed on a pressure column containing 10 g of silica gel (particle size 0.04–0.06 mm) under 0.2–0.4 atmospheres of nitrogen with methylene chloride/ethyl acetate (20:1) as the elution agent. There is obtained benzyl [1-[[2-(o-fluorobenzoyl)-4-nitrophenyl]-methylcarbamoyl]-1-methyl-ethyl]carbamate of melting point 168°–169° (ether/n-hexane).

(c) A solution of 20 mg (0.04 mol) of benzyl [1-[[2-(o-fluorobenzoyl)-4-nitrophenyl]-methylcarbamoyl]-1-methylethyl]carbamate in 0.5 ml of hydrogen bromide/glacial acetic acid (30 percent) is left to stand for 15 minutes, subsequently treated with a 10 percent sodium bicarbonate solution and extracted several times with methylene chloride. The organic phase is dried over sodium sulphate and concentrated, whereupon the residue is chromatographed on a pressure column containing 2 g of silica gel (particle size 0.04–0.06 mm) under 0.2–0.4 atmospheres of nitrogen with methylene chloride as the elution agent. By crystallisation from ether/petroleum ether there is obtained 5-(o-fluorophenyl)-1,3-dihydro-1,3,3-trimethyl-7-nitro-2H-1,4-benzodiazepin-2-one of melting point 127°–129°.

EXAMPLE A

7-Amino-9-chloro-5-(o-fluorophenyl)-1,3-dihydro-1,3,3-trimethyl-2H,1,4-benzodiazepin-2-one can be used as follows as the active substance for the manufacture of pharmaceutical preparations:

| (a) Tablets | 1 tablet contains |
| --- | --- |
| Active substance | 200 mg |
| Microcrystalline cellulose | 155 mg |
| Maize starch | 25 mg |
| Talc | 25 mg |
| Hydroxypropylmethylcellulose | 20 mg |
| | 425 mg |

The active substance is mixed with half of the microcrystalline cellulose and granulated with a 10 percent solution of hydroxypropylmethylcellulose in a mixture of isopropanol and methylene chloride. The granulate is dried, sieved and mixed with the rest of the adjuvants. Then, it is pressed on a press to biplanar tablets having a diameter of 12 mm and a break-bar.

| (b) Capsules | 1 capsule contains |
| --- | --- |
| Active substance | 100.0 mg |
| Maize starch | 20.0 mg |
| Lactose | 95.0 mg |
| Talc | 4.5 mg |
| Magnesium stearate | 0.5 mg |
| | 220.0 mg |

The active substance is mixed with the adjuvants and sieved. After renewed mixing, the resulting capsules fill mass is filled into interlocking gelatin capsules of suitable size on a fully automatic capsule filling machine.

What is claimed is:

1. A compound of the formula

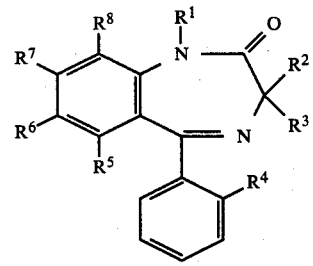

wherein $R^1$ is lower alkyl, lower hydroxyalkyl or lower dialkylaminoalkyl, $R^2$ and $R^3$ each are lower alkyl, $R^4$ is halogen, $R^5$, $R^7$ and $R^8$ each are hydrogen or halogen and $R^6$ is nitro, amino, lower alkylamino, lower dialkylamino or a group of the formula $H_2N-C(CH_3)_2-CO-NH-$, $R^9R^{10}N-CO-NH-$ or

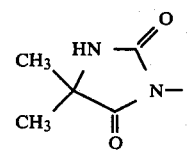

and either $R^9$ is hydrogen or lower alkyl and $R^{10}$ is lower alkyl or lower hydroxyalkyl or $R^9$ and $R^{10}$ together with the nitrogen atom are a heterocycle selected from the group consisting of aziridin-1-yl, pyrrolidin-1-yl, 4-methyl-piperazin-1-yl and morpholin-4-yl and their pharmaceutically acceptable acid addition salts.

2. The compound of claim 1, wherein $R^1$ is methyl.

3. The compound of claims 1 or 2, wherein $R^2$ and $R^3$ both are methyl.

4. The compound of claims 1, 2 or 3, wherein $R^4$ is fluorine or chlorine.

5. The compound of claims 1,2,3 or 4, wherein $R^5$ is hydrogen, chlorine or bromine.

6. The compound of claims 1,2,3,4 or 5, wherein $R^7$ is hydrogen, chlorine or bromine.

7. The compound of claims 1,2,3,4,5 or 6, wherein $R^8$ is hydrogen or chlorine.

8. The compound: 7-Amino-9-chloro-5-(o-fluorophenyl)-1,3-dihydro-1,3,3-trimethyl-2H-1,4-benzodiazepin-2-one.

9. The compound: 7-Amino-6,8-dibromo-5-(o-fluorophenyl)-1,3-dihydro-1,3,3-trimethyl-2H-1,4-benzodiazepin-2-one.

10. The compound: 7-Amino-6,8-dibromo-5-(o-chlorophenyl)-1,3-dihydro-1,3,3-trimethyl-2H-1,4-benzodiazepin-2-one.

11. The compound: 7-Amino-6,8-dichloro-5-(o-chlorophenyl)-1,3-dihydro-1,3,3-trimethyl-2H-1,4-benzodiazepin-2-one.

12. A compound selected from the group consisting of:
1-[6-Bromo-5-(o-chlorophenyl)-2,3-dihydro-1,3,3-trimethyl-2-oxo-1H-1,4-benzodiazepin-7-yl]-2-(2-hydroxyethyl)urea, 7-amino-9-chloro-5-(o-chlorophenyl)-1,3-dihydro-1,3,3-trimethyl-2H-1,4-benzodiazepin-2-one, 1-[5-(o-chlorophenyl)-2,3-dihydro-1,3,3-trimethyl-2-oxo-1H-1,4-benzodiazepin-7-yl]-3-(2-hydroxyethyl)urea, 7-amino-6,8,9-trichloro-1,3-dihydro-5-(o-fluorophenyl)-1,3,3-trimethyl-2H-1,4-benzodiazepin-2-one, 7-amino-8,9-dichloro-5-(o-fluorophenyl)-1,3-dihydro-1,3,3-trimethyl-2H,-1,4-benzodiazepin-2-one.

13. A compound selected from the group consisting of: 7-amino-6-chloro-5-(o-fluorophenyl)-1,3-dihydro-1,3,3-trimethyl-2H-1,4-benzodiazepin-2-one and 2-amino-N-[5-(o-fluorophenyl)-2,3-dihydro-1,3,3-trimethyl-2-oxo-1H-1,4-benzodiazepin-7-yl]-2-methylpropionamide.

* * * * *